United States Patent
Fu

(10) Patent No.: US 11,612,595 B2
(45) Date of Patent: Mar. 28, 2023

(54) COMPOSITIONS AND METHODS FOR TREATING RHEUMATOID ARTHRITIS

(71) Applicant: Generos Biopharma Ltd., Shanghai (CN)

(72) Inventor: Xin-Yuan Fu, Moreno Valley, CA (US)

(73) Assignee: GENEROS BIOPHARMA LTD., Shanghai (CN)

( * ) Notice: Subject to any disclaimer, the term of this patent is extended or adjusted under 35 U.S.C. 154(b) by 592 days.

(21) Appl. No.: 16/613,261

(22) PCT Filed: May 4, 2018

(86) PCT No.: PCT/US2018/031217
§ 371 (c)(1),
(2) Date: Nov. 13, 2019

(87) PCT Pub. No.: WO2018/213027
PCT Pub. Date: Nov. 22, 2018

(65) Prior Publication Data
US 2020/0306235 A1 Oct. 1, 2020

Related U.S. Application Data

(60) Provisional application No. 62/506,698, filed on May 16, 2017.

(51) Int. Cl.
| | |
|---|---|
| *C07D 235/26* | (2006.01) |
| *C07D 401/04* | (2006.01) |
| *C12N 9/22* | (2006.01) |
| *C12N 15/11* | (2006.01) |
| *A61P 19/02* | (2006.01) |
| *A61P 29/00* | (2006.01) |
| *A61P 37/02* | (2006.01) |
| *A61K 31/4406* | (2006.01) |
| *A61K 31/454* | (2006.01) |
| *A61K 31/455* | (2006.01) |
| *A61K 31/7088* | (2006.01) |
| *A61K 45/06* | (2006.01) |
| *A61K 38/46* | (2006.01) |

(52) U.S. Cl.
CPC .......... *A61K 31/454* (2013.01); *A61K 31/455* (2013.01); *A61K 31/7088* (2013.01); *A61K 38/465* (2013.01); *A61P 19/02* (2018.01); *A61P 37/02* (2018.01); *C12N 9/22* (2013.01); *C12N 15/11* (2013.01); *C12N 2310/20* (2017.05); *C12N 2800/80* (2013.01)

(58) Field of Classification Search
CPC ...... C07D 235/26; C07D 401/04; C12N 9/22; C12N 15/11; C12N 2310/20; C12N 2800/80; A61P 19/02; A61P 29/00; A61P 37/02; A61K 31/4406; A61K 31/454; A61K 31/455; A61K 31/7088; A61K 38/465; A61K 45/06
See application file for complete search history.

(56) References Cited

U.S. PATENT DOCUMENTS 8,093,267 B2  1/2012  Augeri et al.

FOREIGN PATENT DOCUMENTS

WO    WO-2016/048247 A    3/2016

OTHER PUBLICATIONS

Notice of Reasons for Rejection dated May 31, 2022 issued in JP 2019-563766, with English translation, 10 pages.
Office Action dated Jul. 13, 2022 issued in CN Application No. 201880045404.9, with English translation, 10 pages.
International Search Report issued in International Application No. PCT/US2018/031217 dated Aug. 31, 2018 (4 total pages).
Miklossy, Gabriella, et al., "Therapeutic modulators of STAT signaling for human diseases", *Nature Reviews Drug Discovery* (2013), vol. 12, pp. 611-629.
Nelson, Erik A., et al., "The STAT5 inhibitor pimozide decreases survival of chronic myelogenous leukemia cells resistant to kinase inhibitors", *Blood* 2011; vol. 117, No. 12, pp. 3421-3429.
Ran, F. Ann, et al., "In vivo genome editing using *Staphylococcus aureus* Cas9", *Nature* (2015), vol. 520 (18 total pages).
Zetsche, Bernd, et al., "Cpf1 Is a Single RNA-Guided Endonuclease of a Class 2 CRISPR-Cas System", *Cell* (2015), vol. 163, pp. 759-771.
Zhou, Wei, et al., "The antipsychotic drug pimozide inhibits cell growth in prostate cancer through suppression of STAT3 activation", *International Journal of Oncology* (2016), vol. 48, pp. 322-328.
Communication pursuant to Rule 164(1) EPC dated Mar. 19, 2021 issued in European Patent Application No. 18801432.8, 14 pages.
Sheng, Wanqiang, et al., "STAT5 programs a distinct subset of GM-CSF-producing T helper cells that is essential for autoimmune neuroinflammation," Cell Research (2014), 24:1387-1402.

*Primary Examiner* — Brenda L Coleman
(74) *Attorney, Agent, or Firm* — Foley & Lardner LLP

(57) ABSTRACT

Disclosed are methods and compositions for treating ore preventing a STAT5-mediated medical condition, e.g., rheumatoid arthritis, in a subject by administering to the subject a therapeutically effective amount of a compound, the compound being a STAT5 inhibitor, or a pharmaceutically acceptable salt of the STAT5 inhibitor, or a solvate of the STAT5 inhibitor, or a prodrug of the STAT5 inhibitor. In one example, the compound used in the methods and compositions is pimozide. In another example, the compound used in the methods and compositions is nicotinohydrazide.

5 Claims, 8 Drawing Sheets p<0.0001; F (4, 41) = 15.35

COMPOSITIONS AND METHODS FOR TREATING RHEUMATOID ARTHRITIS

FIELD OF INVENTION

The invention relates generally to the field of pharmaceutical agents and uses the pharmaceutical agents for disease treatments thereof, specifically the pharmaceutical agents that targets inhibits signal transducer and activator of transcription 5 (STAT5), and uses of the pharmaceutical agents in managing physiological conditions, specifically inflammatory disorders, more specifically rheumatoid arthritis, lupus and multiple sclerosis.

BACKGROUND

Rheumatoid arthritis (RA) is a common type of autoimmune arthritis, and can affect joints, such as the knee, wrist and small joints of the hand. RA is triggered by a faulty immune system attacks the synovium, the resulting inflammation thickens the synovium, which can eventually destroy the cartilage and bone within the joint. The tendons and ligaments that hold the joint together weaken and stretch. Gradually, the joint loses its shape and alignment.

There is no cure for RA. Common therapeutic agents for alleviating RA include: (1) NSAIDs, which relieve pain and reduce inflammation, (2) steroids, such as corticosteroid medications (e.g., prednisone) which reduces inflammation and pain and slow joint damage; (3) disease-modifying antirheumatic drugs (DMARDs), which can slow the progression of rheumatoid arthritis and save the joints and other tissues from permanent damage (examples of DMARDs include methotrexate (Trexall. Otrexup, Rasuvo), leflunomide (Arava), hydroxychloroquine (Plaquenil) and sulfasalazine (Azulfidine)); (4) biologic agents, which are also known as biologic response modifiers, and includes abatacept (Orencia), adalimumab (Humira), anakinra (Kinrect), ccrtolizumab (Cimia), etanercept (Enbrel), golimumab (Simponi), infliximab (Remicade), rituximab (Rituxan), tocilizumab (Actemra) and tofacitinib (Xeljanz).

Signal transducer and activator of transcription 5 (STAT5) refers to two highly related proteins. STAT5A and STAT5B, which are part of the seven-membered STAT family of proteins. STAT5 proteins are involved in cytosolic signaling and in mediating the expression of specific genes. Aberrant STAT5 activity has been shown to be closely connected to a wide range of human cancers, including chronic myclogenous leukemia, acute lymphoblastic leukemia and Hodgkin's lymphoma.

Pimozide is a cell-permeable and orally available diphenylbutylpiperidine class of psychotropic drug with antagonistic activity against DAT (dopamine transporter) as well as several postsynaptic receptors, including D1, D2, D3, D4, α1-/α2-adrenergic, and 5-HT2A receptors, and works by blocking the action of dopamine. Pimozide is a FDA-approved for treating uncontrolled movements (motor tics) or outbursts of words/sounds (vocal tics) in patients with Tourette syndrome when other medicines have not worked.

More recently, Nelson et al. (Blood, 2011; 117(12):3421-9) used a cell-based screen to identify drugs that inhibit STAT-dependent gene expression, and identified pimozide as a STAT5 inhibitor. They found that pimozide decreased STAT5 tyrosine phosphorylation, and decreased the expression of STAT5 target genes and induces cell cycle arrest and apoptosis in Chronic Myeloid Leukemia (CML) cell lines. Specifically, pimozide inhibits the constitutive STAT5 Tyr694 phosphorylation (5 to 10 μM for 3 h) and transcription activity (5 μM for 18 h) in Bcr-Abl+ K562 and KU812 cultures, while exhibiting little activity against IFNα-stimulated STAT1 phosphorylation or LIF-stimulated STAT3 phosphorylation in K562 cells (10 μM 1 h pretreatment).

In addition to pimozide, STAT5 inhibitors also include N'-((4-Oxo-4H-chromen-3-yl)methylene)nicotinohydrazide (nicotinohydrazide), which is a cell-permeable nonpeptidic nicotinoyl hydrazone compound that selectively targets the SH2 domain of STAT5 (IC50=47 μM against STAT5b SH2 domain EPO peptide binding activity), while exhibiting much less effect towards the SH2 domain of STAT1. STAT3, or Lck (IC50>500 μM). Nicotinohydrazide blocks STAT5/STAT5 DNA binding activity in K562 nuclear extract and inhibit IFN-α-stimulated STAT5, but not STAT1 or STAT3, tyrosine phosphorylation in Daudi cells.

BRIEF SUMMARY OF THE INVENTION

In one aspect, the present invention is a method of treating or preventing rheumatoid arthritis in a subject comprising administering to the subject a therapeutically effective amount of a compound, the compound being a STAT5 inhibitor, or a pharmaceutically acceptable salt of the STAT5 inhibitor, or a solvate of the STAT5 inhibitor, or a prodrug of the STAT5 inhibitor. In one embodiment, the compound is pimozide. In another embodiment, the compound is nicotinohydrazide.

In another aspect, the present invention is a method of treating or preventing RA in an anti-TNF non-responder comprising administering to the anti-TNF non-responder a therapeutically effective amount of a compound, the compound being a STAT5 inhibitor, or a pharmaceutically acceptable salt of the STAT5 inhibitor, or a solvate of the STAT5 inhibitor, or a prodrug of the STAT5 inhibitor. In one embodiment, the compound is pimozide. In another embodiment, the compound is nicotinohydrazide.

In still another aspect, the present invention is a method of treating or preventing a STAT5-mediated medical condition in a subject a therapeutically effective amount of a compound, the compound being a STAT5 inhibitor, or a pharmaceutically acceptable salt of the STAT5 inhibitor, or a solvate of the STAT5 inhibitor, or a prodrug of the STAT5 inhibitor. In one embodiment, the compound is pimozide. In another embodiment, the compound is nicotinohydrazide.

In still a further aspect, the present invention is a method of treating or preventing a STAT5-mediated autoimmune disease in a subject a therapeutically effective amount of a compound, the compound being a STAT5 inhibitor, or a pharmaceutically acceptable salt of the STAT5 inhibitor, or a solvate of the STAT5 inhibitor, or a prodrug of the STAT5 inhibitor. In one embodiment, the compound is pimozide. In another embodiment, the compound is nicotinohydrazide.

In some embodiments of each of the above aspect, pimozide may be administered to the subject in an amount between about 0.1 mg/kg of body weight to about 20 mg/kg of body weight per day.

In some embodiments of each of the above aspect, pimozide may be administered to the subject in an amount between about 0.1 mg/kg of body weight to about 1 mg/kg of body weight per day.

In some embodiments of each of the above aspect, pimozide may be administered to the subject in an amount between about 1 mg/kg of body weight to about 5 mg/kg of body weight per day.

In some embodiments of each of the above aspect, pimozide may be administered to the subject in an amount between about 5 mg/kg of body weight to about 10 mg/kg of body weight per day.

In some embodiments of each of the above aspect, the compound may be a pharmaceutically acceptable salt of the STAT5 inhibitor. In other embodiments, the compound may be a solvate of the STAT5 inhibitor. In still other embodiments, the compound may be prodrug of the STAT5 inhibitor. In one embodiment, the compound is pimozide. In another embodiment, the compound is nicotinohydrazide.

In some embodiments of each of the above aspect, STAT5 activity may be inhibited through the steps of: (i) providing a genome editing tool; (ii) delivering the genome editing tool to joint tissue cells; and (iii) editing the STAT5 gene by deleting the entire STAT5 gene, the phosphorylation site of the STAT5 gene, the promoter region of the STAT5 gene, or the SH2 domain of the STAT5 gene. In some instances, the genome editing tool is a CRISPR-CAS9 system.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 7A shows the weight changes of prophylactic groups compared to blank control. FIG. 7B shows the weight change of therapeutic groups compared to blank control.

In FIG. 8A, different chemicals (DMSO as control for Model group, blank group is left untreated) were daily administered intraperitoneally at the indicated doses from the first injection of the collagen agent. In FIG. 8B, different chemicals were daily administered intraperitoneally from the second injection of collagen agent at the indicated doses. Clinical scores were given double-blindly according to the scoring scheme every 2 days.

DETAILED DESCRIPTION OF THE INVENTION

Figure 1A:
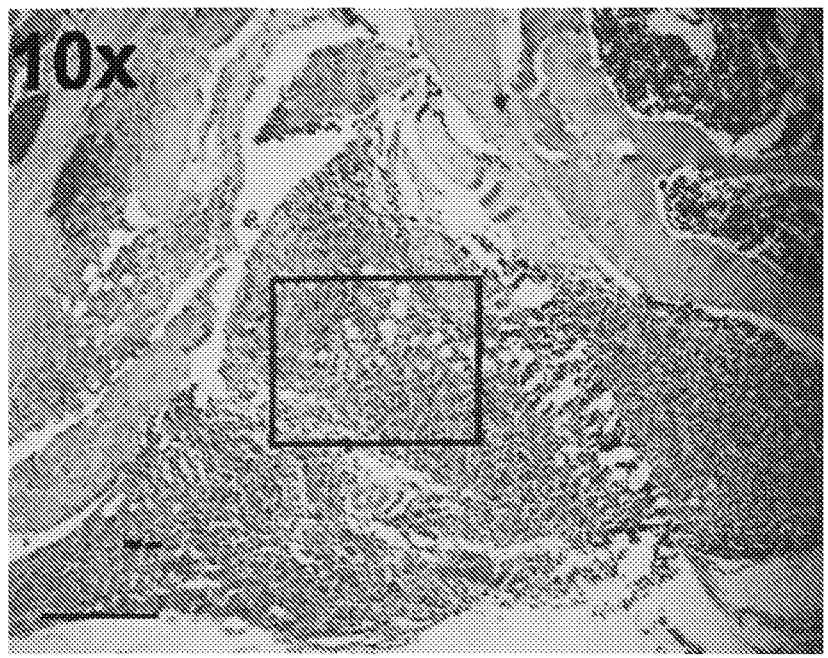
FIG. 1A is a representative section of a microscopic image of H&E staining of a mouse knee with vehicle treatment. The bar in the lower left of the image indicates 200 Mm.

The present disclosure is based, in part, on a new and surprising discovery that STAT5 activity is involved in autoimmune diseases including rheumatoid arthritis, lupus and multiple sclerosis.

In one aspect, the present invention provides a method of treating or preventing rheumatoid arthritis in a subject by administering to the subject a therapeutically effective amount of a STAT5 inhibitor, a therapeutically effective amount of a pharmaceutically acceptable salt of the STAT5 inhibitor, or a solvate of the STAT5 inhibitor, or a prodrug of the STAT5 inhibitor.

In another aspect, the present invention is a method of treating or preventing RA in an anti-TNF non-responder comprising administering to the anti-TNF non-responder a therapeutically effective amount of a compound, the compound being a STAT5 inhibitor, or a pharmaceutically acceptable salt of the STAT5 inhibitor, or a solvate of the STAT5 inhibitor, or a prodrug of the STAT5 inhibitor. The anti-TNF non-responder is resistant or insensitive to TNF drug treatments.

In still another aspect, the present invention is a method of treating or preventing a STAT5-mediated medical condition in a subject a therapeutically effective amount of a compound, the compound being a STAT5 inhibitor, or a pharmaceutically acceptable salt of the STAT5 inhibitor, or a solvate of the STAT5 inhibitor, or a prodrug of the STAT5 inhibitor. A STAT5-mediated medical condition may include rheumatoid arthritis or other diseases such as lupus and multiple sclerosis.

In a further aspect, the present invention is a method of treating or preventing a STAT5-mediated autoimmune disease in a subject a therapeutically effective amount of a compound, the compound being a STAT5 inhibitor, or a pharmaceutically acceptable salt of the STAT5 inhibitor, or a solvate of the STAT5 inhibitor, or a prodrug of the STAT5 inhibitor. The STAT5-mediated autoimmune disease may be rheumatoid arthritis, lupus or multiple sclerosis.

In some embodiments, the STAT5 inhibitor is pimozide, or a pharmaceutically acceptable salt, or a solvate, or a prodrug thereof. The chemical name of pimozide is 1-[1-[4,4-bis(4-fluorophenyl)butyl]-4-piperidinyl]-1,3-dihydro-2H-benzimidazole-2-one under CAS 2062-78-4, with a structure represented below:

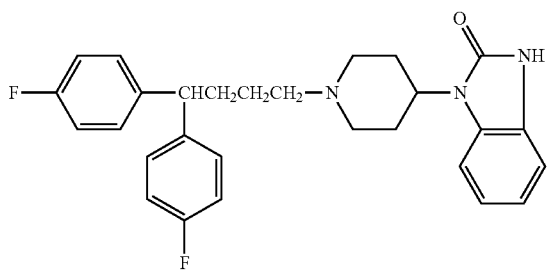

In other embodiments, the STAT5 inhibitor is N'-((4-Oxo-4H-chromen-3-yl)methylene)nicotinohydrazide (nicotinohydrazide) under CAS 285986-31-4, or a pharmaceutically acceptable salt, or a solvate, or a prodrug thereof. The structure is represented below:

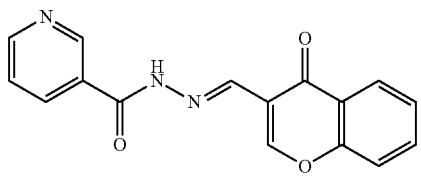 [SMILES: O=C(N/N=C/c1coc2ccccc2c1=O)c1cccnc1]

In another aspect, the present invention provides a method of treating or preventing rheumatoid arthritis in a subject by administering to the subject a composition comprising a therapeutically effective amount of pimozide, a pharmaceutically acceptable salt thereof, a solvate thereof, or a prodrug thereof.

In another aspect, the present invention provides a method of treating or preventing RA in an anti-TNF non-responder in a subject by administering to the subject a composition comprising a therapeutically effective amount of pimozide, a pharmaceutically acceptable salt thereof, a solvate thereof, or a prodrug thereof.

In a further aspect, the present invention provides a kit comprising a therapeutically effective amount of pimozide, a pharmaceutically acceptable salt thereof, a solvate thereof, or a prodrug thereof, and instructions to use the compound.

In a still further aspect, the present invention provides a method of treating or preventing a STAT5-mediated medical condition in a subject by administering to the subject a composition comprising a therapeutically effective amount of pimozide, a pharmaceutically acceptable salt thereof, a solvate thereof, or a prodrug thereof. In some embodiments, the STAT5-mediated medical condition may be rheumatoid arthritis, lupus or multiple sclerosis.

In a still further aspect, the present invention provides a method of treating or preventing a STAT5-mediated autoimmune disease in a subject by administering to the subject a composition comprising a therapeutically effective amount of pimozide, a pharmaceutically acceptable salt thereof a solvate thereof, or a prodrug thereof. In some embodiments, the autoimmune disease may be rheumatoid arthritis, lupus or multiple sclerosis.

In another aspect, the present invention provides a method of treating or preventing rheumatoid arthritis in a subject by administering to the subject a composition comprising a therapeutically effective amount of nicotinohydrazide, a pharmaceutically acceptable salt thereof, a solvate thereof, or a prodrug thereof.

In another aspect, the present invention provides a method of treating or preventing RA in an anti-TNF non-responder in a subject by administering to the subject a composition comprising a therapeutically effective amount of nicotinohydrazide, a pharmaceutically acceptable salt thereof, a solvate thereof, or a prodrug thereof.

In a further aspect, the present invention provides a kit comprising a therapeutically effective amount of nicotinohydrazide, a pharmaceutically acceptable salt thereof, a solvate thereof, or a prodrug thereof, and instructions to use the compound.

In a still further aspect, the present invention provides a method of treating or preventing a STAT5-mediated medical condition in a subject by administering to the subject a composition comprising a therapeutically effective amount of nicotinohydrazide, a pharmaceutically acceptable salt thereof, a solvate thereof, or a prodrug thereof. In some embodiments, the STAT5-mediated medical condition may be rheumatoid arthritis, lupus or multiple sclerosis.

In a still further aspect, the present invention provides a method of treating or preventing a STAT5-mediated autoimmune disease in a subject by administering to the subject a composition comprising a therapeutically effective amount of nicotinohydrazide, a pharmaceutically acceptable salt thereof, a solvate thereof, or a prodrug thereof. In some embodiments, the autoimmune disease may be rheumatoid arthritis, lupus or multiple sclerosis.

In still further instances, as a method for treatment, prevention, or delaying the onset of RA a genome editing tool may be used to delete the entire STAT5 gene, the phosphorylation site of the STAT5 gene, the promoter region of the STAT5 gene, or the SH2 domain of the STAT5 gene in joint tissue cells. The genome editing tool can be any genome editing tool as long as it can be used to target the specific regions of STAT5 gene and can be delivered to cells of interest. One example of such genome editing tool is the CRISPR-CAS9 system as described in Ran, F. et al. In vivo genome editing using *Staphylococcus aureus* Cas9, Nature (2015). Another example of such genome editing tool is the CRISPR-Cpf1 system as described in Zetsche et al., Cpf1 Is a Single RNA-Guided Endonuclease of a Class 2 CRISPR-Cas System, Cell (2015).

In still further instances, as a method for treating or preventing a STAT5-mediated medical condition, a genome editing tool may be used to delete the entire STAT5 gene, the phosphorylation site of the STAT5 gene, the promoter region of the STAT5 gene, or the SH2 domain of the STAT5 gene in joint tissue cells. The genome editing tool can be any genome editing tool as long as it can be used to target the specific regions of STAT5 gene and can be delivered to cells of interest. One example of such genome editing tool is the CRISPR-CAS9 system as described in Ran, F. et al. In vive genome editing using *Staphylococcus aureus* Cas9, Nature (2015). Another example of such genome editing tool is the CRISPR-Cpf1 system as described in Zectsche et al., Cpf1 Is a Single RNA-Guided Endonuclease of a Class 2 CRISPR-Cas System, Cell (2015).

In still further instances, a method for treating or preventing RA in an anti-TNF non-responder, a genome editing tool may be used to delete the entire STAT5 gene, the phosphorylation site of the STAT5 gene, the promoter region of the STAT5 gene, or the SH2 domain of the STAT5 gene in joint tissue cells. The genome editing tool can be any genome editing tool as long as it can be used to target the specific regions of STAT5 gene and can be delivered to cells of interest. One example of such genome editing tool is the CRISPR-CAS9 system as described in Ran, F. et al. In vive genome editing using *Staphylococcus aureus* Cas9, Nature (2015). Another example of such genome editing tool is the CRISPR-Cpf1 system as described in Zetsche et al., Cpf1 Is a Single RNA-Guided Endonuclease of a Class 2 CRISPR-Cas System, Cell (2015).

In still further instances, as a method for treatment, prevention, or delaying the onset of a STAT5-mediated autoimmune disease, a genome editing tool may be used to delete the entire STAT5 gene, the phosphorylation site of the STAT5 gene, the promoter region of the STAT5 gene, or the SH12 domain of the STAT5 gene in joint tissue cells. The genome editing tool can be any genome editing tool as long as it can be used to target the specific regions of STAT5 gene and can be delivered to cells of interest. One example of such genome editing tool is the CRISPR-CAS9 system as described in Ran, F. et al. In vive genome editing using *Staphylococcus aureus* Cas9, Nature (2015). Another example of such genome editing tool is the CRISPR-Cpf1 system as described in Zetsche et al., Cpf1 Is a Single RNA-Guided Endonuclease of a Class 2 CRISPR-Cas System, Cell (2015).

The terms "a," "an," and "the" and similar references in the context of this disclosure to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the teachings and does not pose a limitation on the scope of the claims. No language in the specification should be construed as indicating any non-claimed element as essential to the practice of the present teachings.

The terms "comprise," "comprises," "comprising," "include," "includes". "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "treating" or "treatment" of a condition, disorder, or disease as used herein means alleviation or amelioration of one or more symptoms of the condition, disorder or disease, diminishment of extent of the condition, disorder or disease, stabilization (i.e., not worsening) of the condition, disorder or disease, delay or slowing of progression of the condition, disorder, or disease, and/or amelioration or palliation of the state of the condition, disorder or disease. The term can also mean prolonging survival as compared to expected survival if not receiving treatment.

The terms "prevent," "preventing," and "prevention" refer to the total or partial inhibition of the development, recurrence, onset or spread of a STAT5-mediated disease and/or symptom related thereto, resulting from the administration of a therapy or combination of therapies provided herein (e.g., a combination of prophylactic or therapeutic agents, such as pimozide).

As used herein, the term "prophylactic agent" refers to any agent that can totally or partially inhibit the development, recurrence, onset or spread of a STAT5-mediated disease and/or symptom related thereto in a subject. In certain embodiments, the term "prophylactic agent" refers to pimozide. Preferably, a prophylactic agent is an agent which is known to be useful to or has been or is currently being used to prevent a STAT5-mediated disease and/or a symptom related thereto or impede the onset, development, progression and/or severity of a STAT5-mediated disease and/or a symptom related thereto.

In an embodiment, the prophylaxis prevents the onset of the disease or condition or of the symptoms of the disease or condition. In one embodiment, the prophylactic treatment prevents the worsening, or onset, of the disease or condition. In one embodiment, the prophylactic treatment prevents the worsening of the disease or condition.

The term "therapeutically effective amount as used herein means the amount of a compound that, when administered to a subject for treating a state, disorder, or condition, is sufficient to effect such treatment. The "therapeutically effective amount" will vary depending on the compound, the disease and its severity and the age, weight, physical condition, and responsiveness of the mammal to be treated.

The term "subject" as used herein, refers to an animal, preferably a mammal, who is in the need of treatment of a STAT5-mediated medical condition, e.g., rheumatoid arthritis. The term subject may be interchangeably used with the term patient in the context of the present disclosure. The term "mammal" refers to a warm-blooded animal that has or is at risk of developing a disease described herein and includes, but is not limited to, guinea pigs, dogs, cats, rats, mice, hamsters, and primates, including humans.

The phrase "pharmaceutically acceptable" indicates that the substance or composition is compatible chemically and/or toxicologically with the other ingredients comprising a formulation, and/or the mammal being treated therewith.

The phrase "pharmaceutically acceptable salt," unless otherwise indicated, includes salts that retain the biological effectiveness of the corresponding free acid or base of the specified compound and are not biologically or otherwise undesirable. Examples of pharmaceutically acceptable salts include those salts prepared by reaction of the compounds of the present disclosure with a mineral or organic acid or an inorganic base, such salts including, but not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, captylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenroates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propunesulfonates, naphthalene-1-sulfonates, naphthalene-2-sulfonates, and mandelates. Since a single compound of the present disclosure may include more than one acidic or basic moiety, the compounds of the present disclosure may include mono, di or tri-salts in a single compound.

The term "prodrug" refers to a compound that may be converted under physiological conditions or by solvolysis to the specified compound or to a salt of such compound.

The compounds of the present disclosure may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoncal, intrapulmonary and intranasal. It will be appreciated that the route used may vary with, for example, the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

To use a compound of the present disclosure for therapeutic treatment of mammals including humans, it can be formulated in accordance with standard pharmaceutical practice as a pharmaceutical composition. Accordingly, there is provided a pharmaceutical composition comprising a compound of the present disclosure in association with a pharmaceutically acceptable diluent or carrier.

The pharmaceutical compositions of the invention are formulated, dosed and administered in a fashion, i.e., amounts, concentrations, schedules, course, vehicles and route of administration, consistent with good medical practice. Factors for consideration in this context include the disorder being treated, the mammal being treated, the clinical condition of the individual patient, the cause of the disorder, the site of delivery of the agent, the method of administration, the scheduling of administration, and other factors known to medical practitioners. The therapeutically effective amount of the compound to be administered will be governed by such considerations, and is the minimum amount necessary to ameliorate or treat the disorder. The compound of the present disclosure can be formulated into pharmaceutical dosage forms to provide an easily controllable dosage of the drug and to enable patient compliance with the prescribed regimen.

Pharmaceutical formulations of the compounds of the present disclosure may be prepared for various routes and types of administration. For example, a compound of the present disclosure having the desired degree of purity may optionally be mixed with pharmaceutically acceptable diluents, carriers, excipients or stabilizers in the form of a lyophilized formulation, a milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The formulations may be prepared using conventional dissolution and mixing procedures. For example, the bulk drug substance (i.e., a compound of the present disclosure or stabilized form of the compound) can be dissolved in a suitable solvent in the presence of one or more excipients.

The carrier, diluent or excipient used will depend upon the means and purpose for which the compound of the present disclosure is being applied.

Solvents can be generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride, benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, argirune, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations may also include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present disclosure or pharmaceutical composition thereof) or aid in the manufacturing of the pharmaceutical product (i.e., medicament).

The active pharmaceutical ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). A "liposomc" is a small-vesicle composed of various types of lipids, phospholipids and/or surfactant which is useful for delivery of a drug to a mammal. The components of the liposome are commonly arranged in a bilayer formation, similar to the lipid arrangement of biological membranes.

Sustained-release preparations of compounds of the present disclosure invention can be prepared. Suitable examples of sustained-release preparations include semipermeable matrices of solid hydrophobic polymers containing a compound of the present disclosure, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers.

The pharmaceutical compositions of the present disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed including synthetic mono- or diglycerides. In addition, fatty acids such as oleic acid may likewise be used in the preparation of injectables.

Pharmaceutical compositions of the present disclosure suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compositions of the invention may also be formulated in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder)

Suitable pharmaceutically-acceptable excipients for a tablet formulation include, for example, inert diluents such as lactose, sodium carbonate, calcium phosphate or calcium carbonate, granulating and disintegrating agents such as corn starch or alginic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be formulated in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethylencoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as *arachis* oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the present disclosure may also be in the form of oil-in-water emulsions. The oily phase may be a vegetable oil, such as olive oil or *arachis* oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols. Formulations suitable for vaginal administration may be presented as pessaries, tampons, creams, gels, pastes, foams or spray formulations containing in addition to the active ingredient such carriers as are known in the art to be appropriate.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for transdermal administration may be in the form of those transdermal skin patches that are well known to those of ordinary skill in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

The pharmaceutical composition (or formulation) for application may be packaged in a variety of ways depending upon the method used for administering the drug. For example, an article for distribution can include a container having deposited therein the pharmaceutical formulation in an appropriate form. Suitable containers are well known to those skilled in the an and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides compositions comprising at least one active ingredient as above defined together with a pharmaceutical carrier therefore. Pharmaceutical carriers are materials useful for administering the composition and may be solid, liquid or gaseous materials which are otherwise inert or acceptable in the pharmaceutical an and are compatible with the active ingredient. These pharmaceutical compositions may be administered parenterally, orally or by any other desired route.

The amount of pimozide used in the disclosed methods that is combined with one or more excipients to produce a single dosage form will necessarily vary depending upon the subject treated, the severity of the disorder or condition, the rate of administration, the disposition of the compound and the discretion of the prescribing physician. In one embodiment, a suitable amount of a compound of this invention is administered to a mammal in need thereof.

Administration in one embodiment occurs in an amount between about 0.001 mg/kg of body weight to about 60 mg/kg of body weight per day.

In another embodiment, administration occurs in an amount between about 0.5 mg/kg of body weight to about 40 mg/kg of body weight per day.

In another embodiment, administration occurs in an amount between about 1 mg/kg of body weight to about 20 mg/kg of body weight per day.

In another embodiment, administration occurs in an amount between about 1 mg/kg of body weight to about 5 mg/kg of body weight per day.

In another embodiment, administration occurs in an amount between about 5 mg/kg of body weight to about 10 mg/kg of body weight per day.

In a further embodiment, administration occurs in an amount between about 10 mg/kg of body weight to about 15 mg/kg of body weight per day.

In another embodiment, administration occurs in an amount between about 15 mg/kg of body weight to about 20 mg/kg of body weight per day.

In a further embodiment, administration occurs in an amount between about 20 mg/kg of body weight to about 25 mg/kg of body weight per day.

In another embodiment, administration occurs in an amount between about 25 mg/kg of body weight to about 30 mg/kg of body weight per day.

In another embodiment, administration occurs in an amount between about 30 mg/kg of body weight to about 35 mg/kg of body weight per day.

In another embodiment, administration occurs in an amount between about 35 mg/kg of body weight to about 40 mg/kg of body weight per day.

In some instances, dosage levels below the lower limit of the aforesaid range may be more than adequate, while in other cases still larger doses may be employed without causing any harmful side effect, provided that such larger doses are first divided into several small doses for administration throughout the day.

Example 1. Efficacy Study of Pimozide in RA Treatment in Mice

This example describes a method of RA treatment with pimozide in a AIA mouse model.

The right knees of fourteen mice (C57BL/6) were immunized with mBSA injection on the right knee to induce arthritis, while the left knees were used as control. Nine of the mice was then treated with pimozide. Specifically, pimozide was dissolved in DMSO at a concentration of 50 mg/ml, and then diluted in 30% PEG300 (Sigma) for intraperitoneal injection at 10 mg/kg dose. The remaining five mice were treated with vehicle DMSO that is diluted in 30% PEG300 for intraperitoneal injection. After 7 days, the mice were sacrificed and knees were dissected and fixed in 10% formalin and decalcified in 5% formic acid before dehydration and embedding in paraffin followed by standard hematoxylin and eosin (H&E) stain procedure.

Figure 1B:
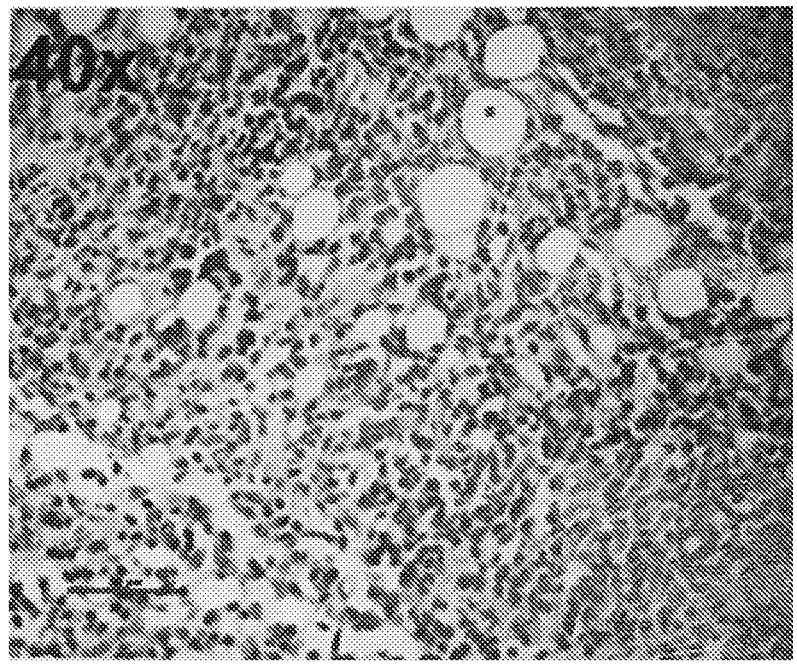
FIG. 1B is an enlarged view of the rectangular area marked in FIG. 1A. The bar in the lower left of the image indicates 50 μm.
Figure 1C:
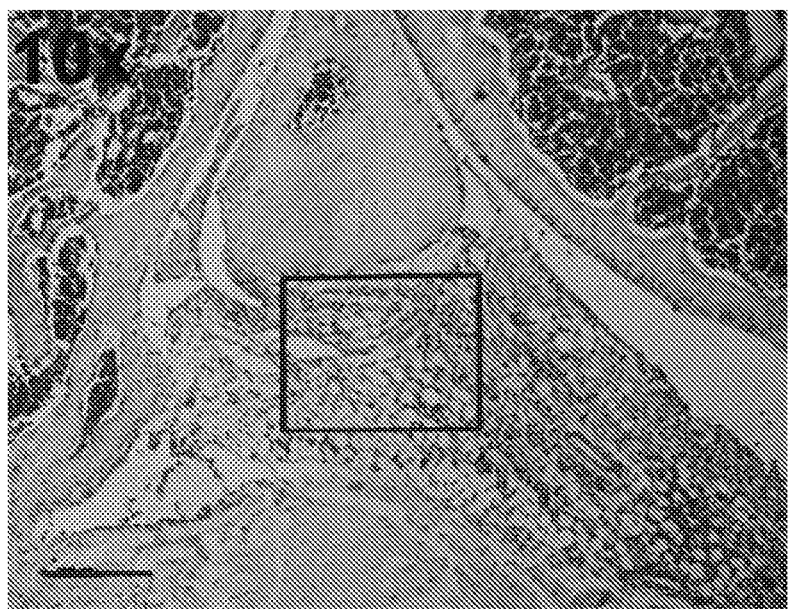
FIG. 1C is a representative section of a microscopic image of H&E staining of a mouse knee treated with pimozide. The bar in the lower left of the image indicates 200 μm.
Figure 1D:
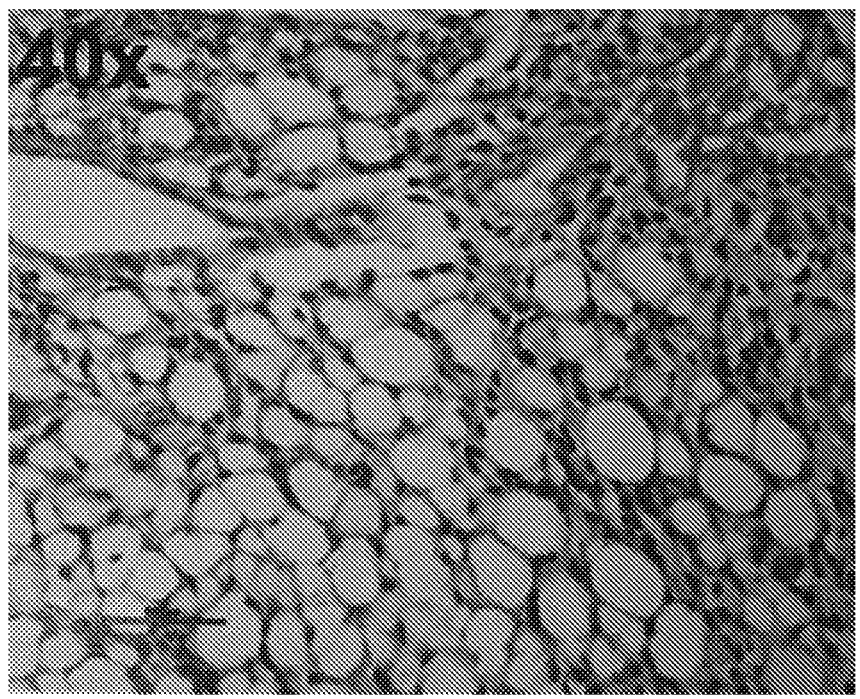
FIG. 1D is an enlarged view of the rectangular area marked in FIG. 1C. The bar in the lower left of the image indicates 50 μm.

FIGS. 1A-1D showed that pimozide-treated knee samples had reduced infiltration of immune cells in knee cavity after RA induction. As shown in FIG. 1A and FIG. 1B (showing magnified photo of the boxed area in FIG. 1A), immune cells infiltrated the tissue of the arthritis-induced knees from untreated mice. In contrast, as shown in FIG. 1C and FIG. 1D (showing magnified photo of the boxed area in FIG. 1A), much less immune cells infiltrated the tissue of the arthritis-induced knees from pimozide treated mice.

Figure 2:
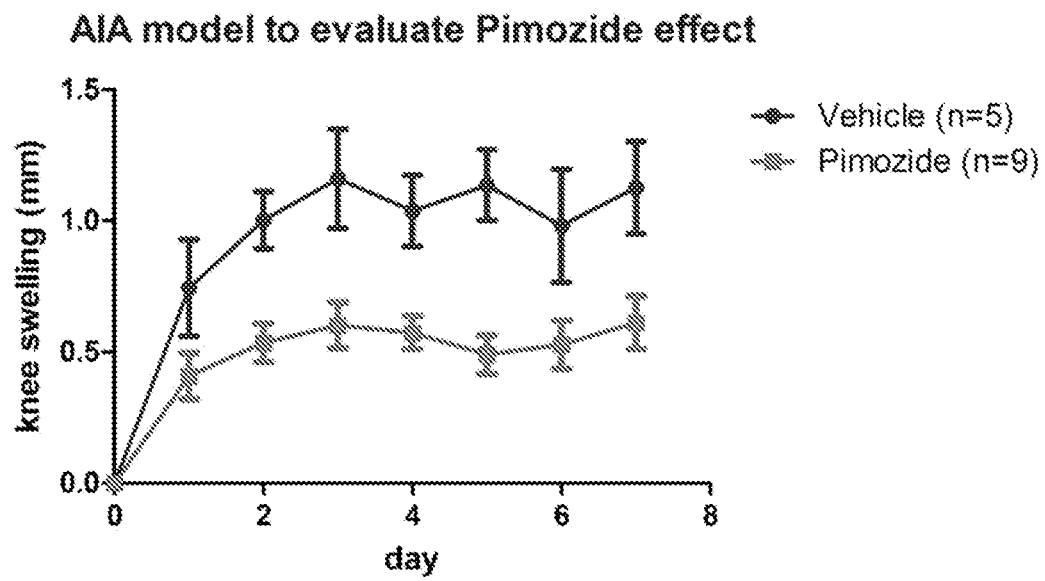
FIG. 2 is a graph showing a graph depicting the knee diameter differences between the vehicle group and the group treated with pimozide in AIA induced mice models. The error bar represents the standard error of the mean. The p value is 0.0004.

FIG. 2 showed that after arthritis induction injection, the knee diameter differences (between the right knee and the left knee of each mouse) in the pimozide-treated group were significantly smaller than the vehicle group. Pimozide-treatment reduced knee swelling, leading to the smaller knee diameter differences between the arthritis-induced right knees and the control left knees. The difference was statistically significant as the p-value was 0.0004.

Example 2. Efficacy Study of Pimozide in RA Treatment in Rats

This example describes the use of pimozide in treating RA in AIA model rats.

Figure 3:
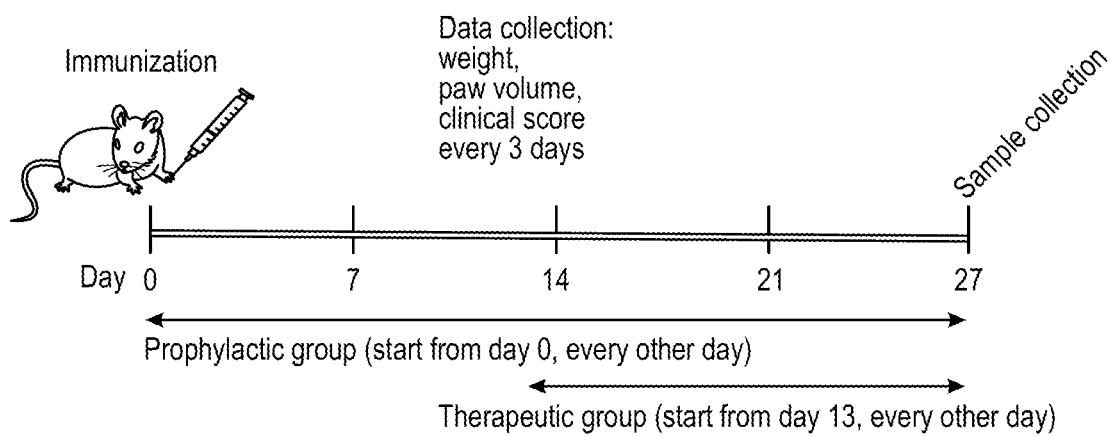
FIG. 3 is a graph illustrating the treatment scheme in an adjuvant-induced arthritis (AIA) rat model. In the prophylactic group, treatment starts from day 0 and administered every other day. In the therapeutic group, treatment starts from day 13 and was administered every other day.

Three groups (10 rats in each group) of female rats (age 8 weeks) were subject to AIA model induction and then to different treatment schemes. See FIG. 3. Specifically, 100 ug mBSA mixed with CFA was injected s.c. to flank near tail, and one dose of B. pertusiss was injected i.p. the next day to boost the immune reaction. The first of the three groups of rats were treated with DMSO (Vehicle). The second of the three groups of rats were treated with pimozide (Sigma-Aldrich) 10 mg/kg of body weight (same unit are used throughout this application) in 30% PEG300 solution via intraperitoneal injection with collagen injection starting from day 7 (Therapeutic). The last of the three groups of rats were treated with pimozide (Sigma-Aldrich) 10 mg/kg in 30% PEG300 solution via intraperitoneal injection either with collagen injection starting from day 0. As a control, a fourth group of female rats (5 rats) were spared the AIA model induction and were not treated. The inventors collected data of the weight, paw volume, and clinical scores every three days and performed statistic analysis.

The clinical scores were derived according to the scheme in Table 1.

TABLE 1

Scoring systems to evaluate arthritis severity

| Score | Clinical signs |
| --- | --- |
| 0 | No erythema or swelling |
| 1 | Slight erythema and swelling in one of the toes or fingers |
| 2 | Erythema and swelling in more than one toe or finger or mild swelling extending from the ankle to the mid-foot |
| 3 | Eryghema and severe swelling in the ankle or wrist |
| 4 | Complete erythema and swelling in toe or fingers and ankle or wrist, and inability to bend the ankle or wrist |

The method used in the statistic analysis was Student's t test, unpaired, two-tailed analysis.

Figure 4:
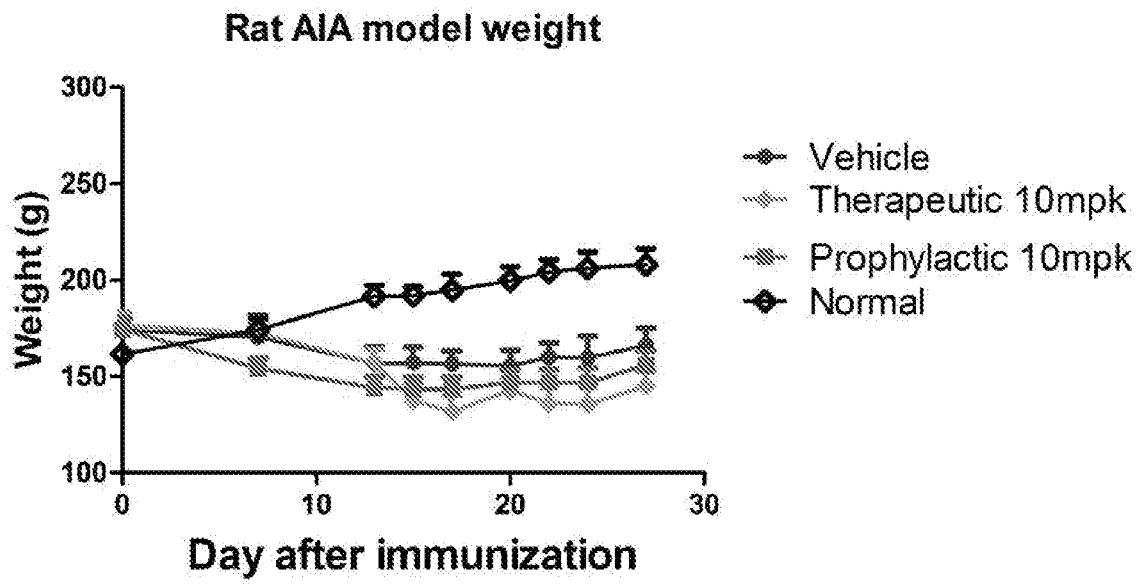
FIG. 4 is a graph depicting weight changes in four groups of rat AIA models under different treatment schemes. Vehicle refers to the group of AIA model rats treated with DMSO. Therapeutic refers to the group of AIA model rats treated with pimozide (Sigma-Aldrich) 10 mg/kg in 30% PEG300 solution starting from day 13. Prophylactic refers to the group of AIA model rats treated with pimozide (Sigma-Aldrich) 10 mg/kg in 30% PEG300 solution starting from day 0. Normal refers to the group of rats without AIA model inducement.

As shown in FIG. 4, the AIA induced rats showed a similar trend of weight changes after the treatments. No significant difference was seen between the three groups: Vehicle. Therapeutic and Prophylactic at each time point.

Figure 5:
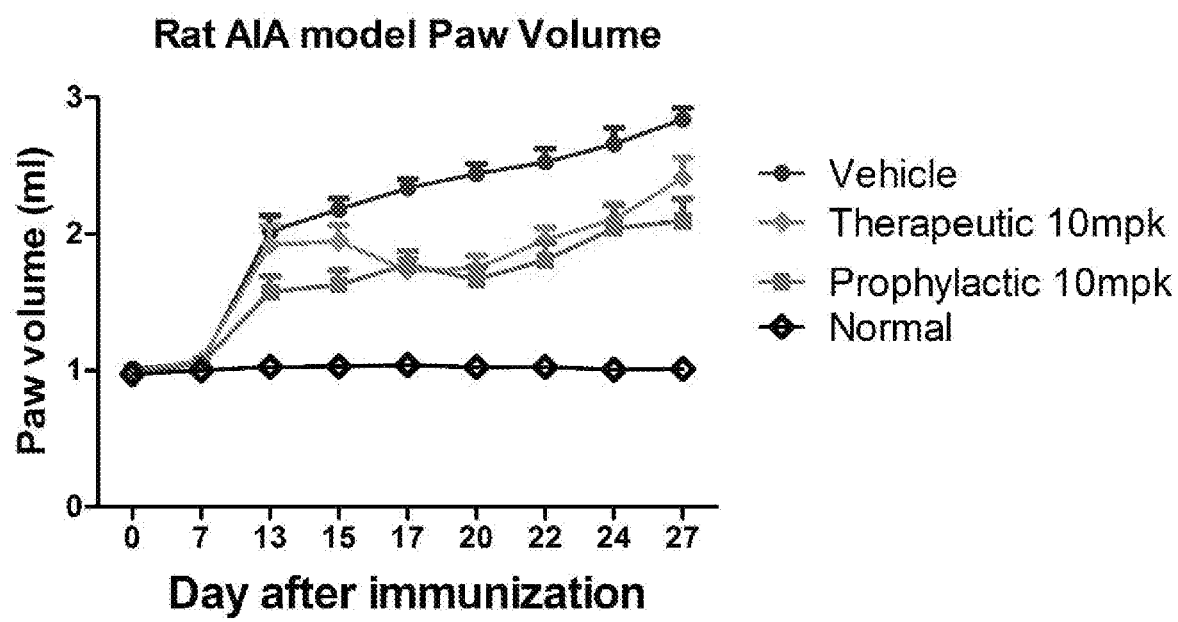
FIG. 5 is a graph depicting paw volume changes in four groups of rat AIA models under different treatment schemes. Vehicle refers to the group of ALA model rats treated with DMSO. Therapeutic refers to the group of AIA model rats treated with pimozide (Sigma-Aldrich) 10 mg/kg in 30% PEG300 solution starting from day 13. Prophylactic refers to the group of AIA model rats treated with pimozide (Sigma-Aldrich) 10 mg/kg in 30% PEG300 solution starting from day 0. Normal refers to the group of rats without AIA model inducement.

However, as shown in FIG. 5, the paw volume in the therapeutic group was significantly decreased from the Vehicle group starting from day 17. $P<0.01$ at day 17, 20, 22, and 24. $P<0.05$ at day 27.

Similarly the paw volume in the prophylactic group was also significantly decreased from the Vehicle group starting from day 13. $P<0.05$ at day 13. $P<0.01$ at day 15, 17, 20, 22, 24 and 27.

Figure 6:
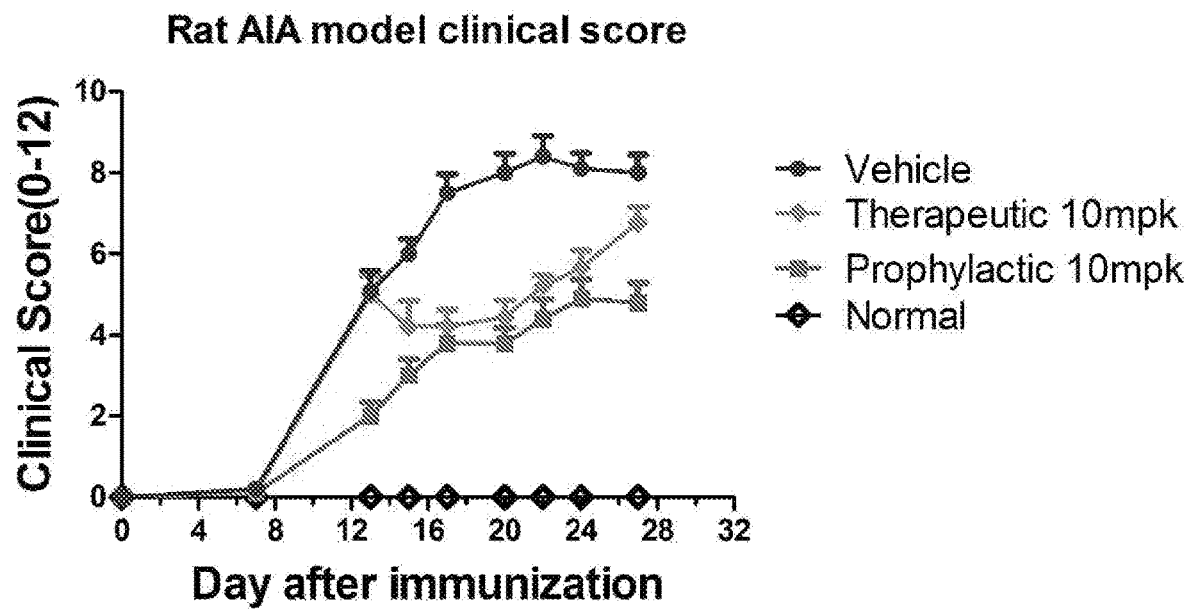
FIG. 6 is a graph depicting clinical score changes in four groups of rat AIA models under different treatment schemes. Vehicle refers to the group of AIA model rats treated with DMSO. Therapeutic refers to the group of AIA model rats treated with pimozide (Sigma-Aldrich) 10 mg/kg in 30% PEG300 solution starting from day 13. Prophylactic refers to the group of AIA model rats treated with pimozide (Sigma-Aldrich) 10 mg/kg in 30% PEG300 solution starting from day 0. Normal refers to the group of rats without AIA model inducement.

The clinical scores showed a patient similar to paw value. As shown in FIG. 6, the clinical score in the therapeutic group was significantly decreased from the Vehicle group starting from day 17. $P<0.05$ at day 15. $P<0.01$ at day 17, 20, 22, and 24.

The clinical score in the prophylactic group was also significantly decreased from the Vehicle group starting from day 13. $P<0.01$ at day 13, 15, 17, 20, 22, 24 and 27.

Example 3. Efficacy Study of Nicotinohydrazide in RA in Mice

This example describes the use of nicotinohydrazide in treating RA in collagen-induced arthritis (CIA) model mice.

Eight of nine groups (10 mice in each group) of male DBA/1J mice (age 9-10 weeks. H-2q haplotype) were subject to CIA model induction and then to different treatment schemes. The group of mice without CIA model induction was used as a control (Blank). Specifically, Bovine type II collagen (Chondrex) was mixed with Freund's complete adjuvant (CFA) (Sigma) and injected s.c. to flank near tail of the mice twice (the second injection was made 21 days after the first injection) to create CIA model mice. The eight groups of CIA model mice were separated into four prophylactic groups and four therapeutic groups, with each group subjected to different treatments.

In the four prophylactic groups, daily treatments started from the date when the first CIA induction injection was made. The first of the four prophylactic groups of CIA model mice were treated with 30% PEG300 (containing 4% DMSO-all 30% PEG300 in the application contains 4% DMSO) solution via intraperitoneal injection as controls (Model). The second of the four prophylactic groups of CIA model mice were treated with nicotinohydrazide (Calbiochem) 10 mg/kg in 30% PEG300 solution via intraperitoneal injection (573108 10 mg/kg). The third of the four prophylactic groups of CIA model mice were treated with nicotinohydrazide (Calbiochem) 5 mg/kg in 30% PEG300 solution via intraperitoneal injection (573108 5 mg/kg). The last of the four prophylactic groups of CIA model mice were treated with Tofacitinib (Selleckchem) 5 mg/kg in 30% PEG300 solution via intraperitoneal injection (Tofacitinib 5 mg/kg).

In the four therapeutic groups, daily treatments started from the date when the second CIA induction injection was made. The first of the four therapeutic groups of CIA model mice were treated with 30% PEG300 solution via intraperitoneal injection as controls (Model). The second of the four therapeutic groups of CIA model mice were treated with nicotinohydrazide (Calbiochem) 10 mg/kg in 30% PEG300 solution via intraperitoneal injection (573108 10 mg/kg). The third of the four therapeutic groups of CIA model mice were treated with nicotinohydrazide (Calbiochem) 5 mg/kg in 30% PEG300 solution via intraperitoneal injection (573108 5 mg/kg). The last of the four therapeutic groups of CIA model mice were treated with Tofacitinib (Selleckchem) 5 mg/kg in 30% PEG300 solution via intraperitoneal injection (Tofacitinib 5 mg/kg).

The inventors collected data of the weight, and clinical scores of the mice every 2-3 days and performed statistic analysis. The method used in the statistic analysis was Student's t test, unpaired, two-tailed analysis.

The clinical scores were derived according to the scheme in Table 2.

TABLE 2

Scoring system to evaluate arthritis severity

| Severity score | Degree of inflammation |
|---|---|
| 0 | No evidence of erythema and swelling |
| 1 | Erythema and mild swelling confied to the tarsals or ankle joint |
| 2 | Erythema and mild swelling extending from the ankle to the tarsals |
| 3 | Erythema and moderate swelling extending from the ankle to the metatarsal joints |
| 4 | Erythema and severe swelling encompass the ankle, foot and digits or ankylosis of the limb |

Figure 7A:
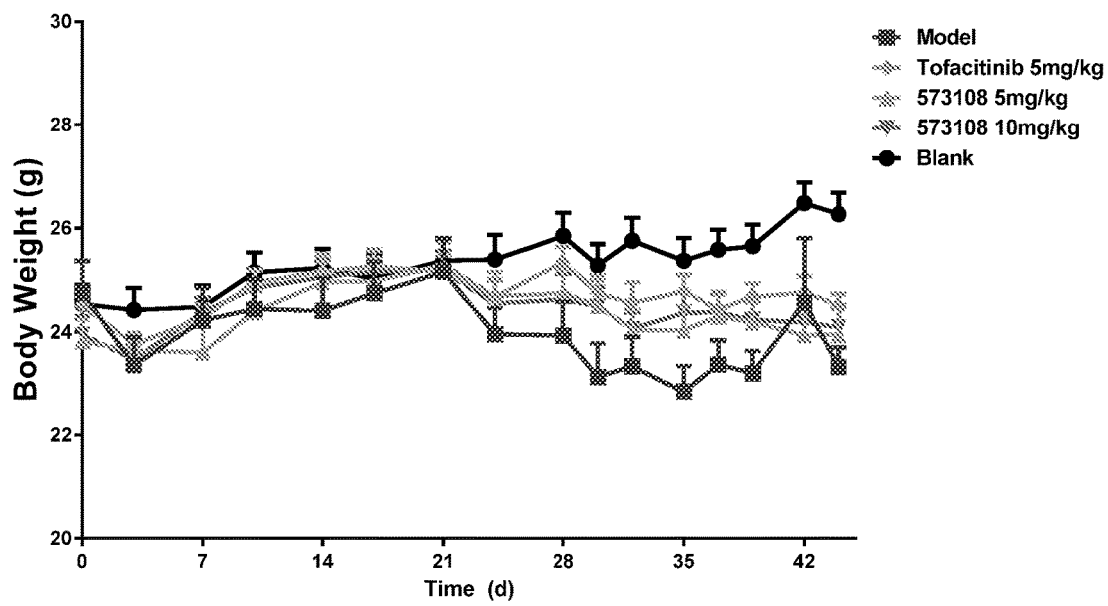
FIGS. 7A and 7B show graphs depicting weight changes in five groups of mouse CIA models under different treatment schemes. DBA/1 mice were randomly divided into 9 groups with 10 mice each group. On day 0 and 21, all of them except blank control group were inoculated with 50 ul collagen plus CFA mixture subcutaneously at back flank near tail. The weights of all 90 mice were monitored 3 times a week throughout the experiment.

As shown in FIG. 7A, the CIA induced mice in the four prophylactic groups showed a similar trend of weight changes after the treatments. All mice had decreased weight after the second CIA induction injection at day 21. Results of statistic analysis of the trend of weight changes between between the four groups: Model, 573108 10 mg/kg, 573108 5 mg/kg, and Tofacitinib 5 mg/kg, were as follows: Model vs Tofacitinib 5 mg/kg p=0.0130 *; Model vs 573108 10 mg/kg p=0.32; Model vs 573108 5 mg/kg p=0.4638; Tofacitinib 5 mg/kg vs 573108 10 mg/kg p=0.0207; and Tofacitinib 5 mg/kg vs 573108 5 mg/kg p=0.0136*. In contrast, mice in the Blank group did not show decreased weight after the second CIA induction injection at day 21. * means statistically significant.

Figure 7B:
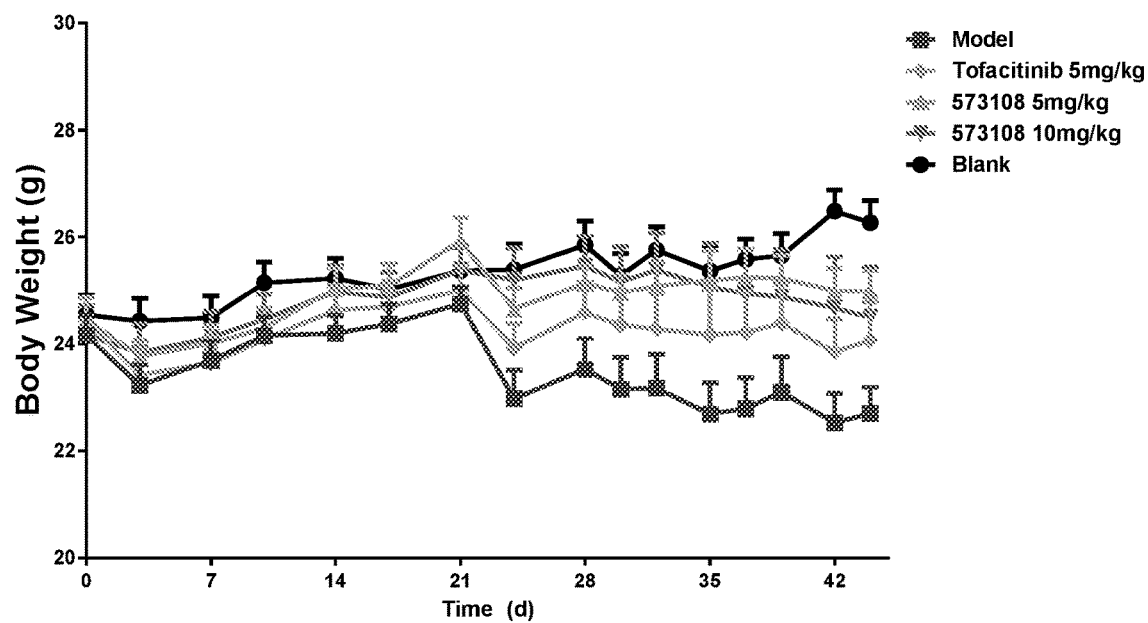

As shown in FIG. 7B, the CIA induced mice in the four therapeutic groups showed a similar trend of weight changes after the treatments. All mice had decreased weight after the second CIA induction injection at day 21. Results of statistic analysis of the trend of weight changes between the four groups: Model, 573108 10 mg/kg, 573108 5 mg/kg, and Tofacitinib 5 ms/kg were as follows: Model vs Tofacitinib 5 mg/kg p=0.0005*, Model vs 573108 10 mg/kg p<0.0001 *; Model vs 573108 5 mg/kg p<0.0001*; Tofacitinib 5 mg/kg vs 573108 10 mg/kg p=0.000K9*; Tofacitinib 5 mg/kg vs 573108 5 mg/kg p=0.0006***. In contrast, mice in the Blank group did not have decreased weight after the second CIA induction injection at day 21.

Figure 8A:
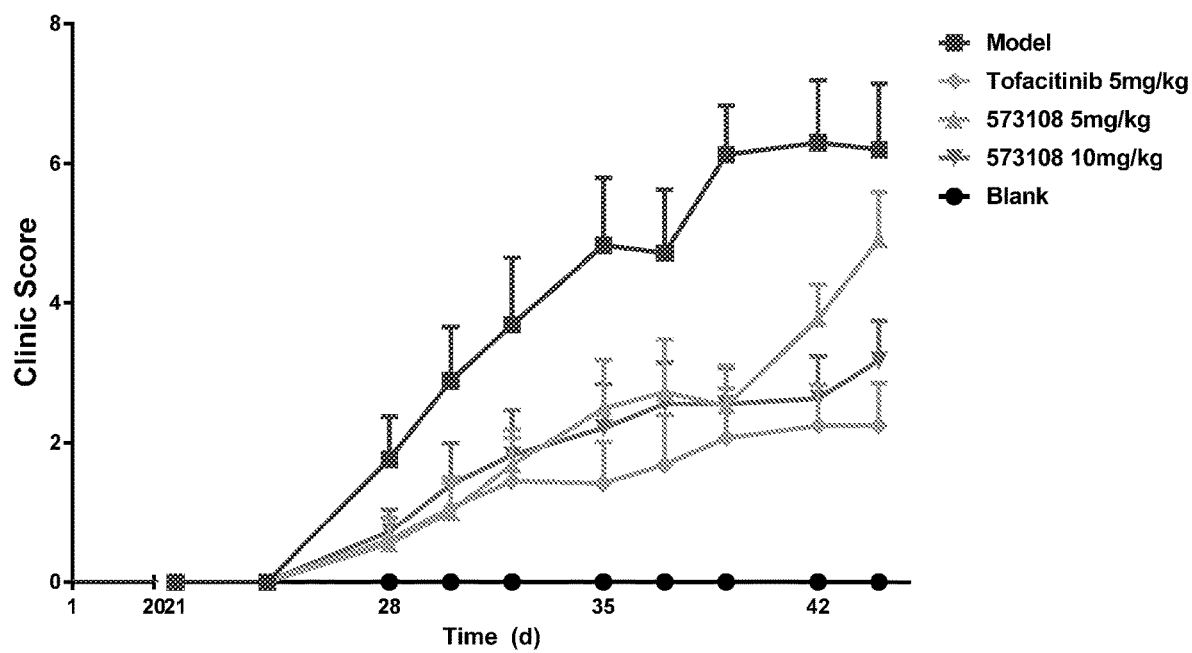
FIGS. 8A and 8B show graphs depicting clinical score changes in four groups of CIA mouse models under different treatment schemes.
Figure 8B:
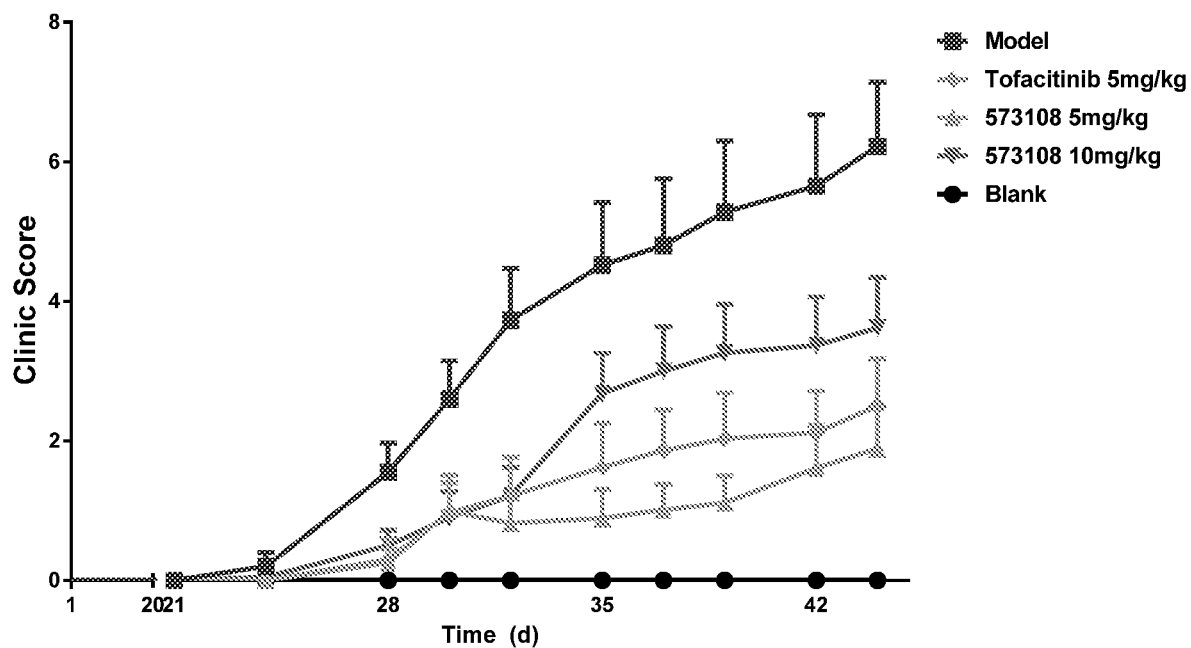
Figure 9A:
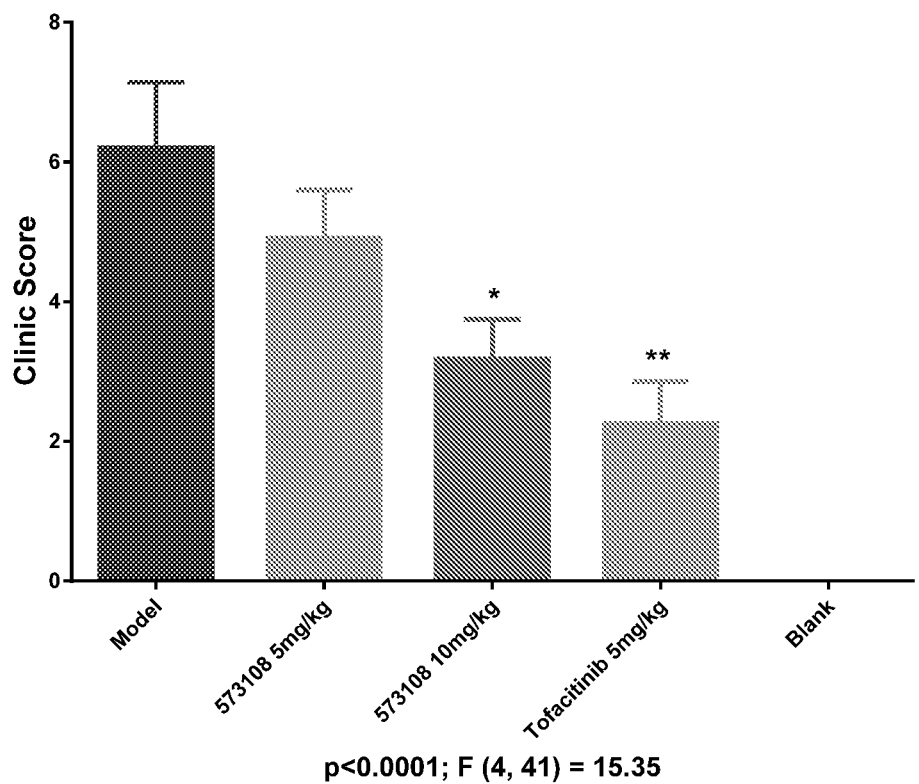
FIGS. 9A and 9B show graphs of clinical scores at day 44 for each group, the overall difference analyzed by ANOVA is significant $p<0.0001$, while the p value between Model and each individual group is labeled above the bar * $p<0.05$, ** $p<0.01$.

As shown in FIG. 8A, in the CIA induced mice in the four prophylactic groups, compared to the negative controls without treatment (Model), treatment with nicotinohydrazide (573108 10 mg/kg and 573108 5 mg/kg) led to reduced clinical scores similar to the treatment with Tofacitinib (Tofacitinib 5 mg/kg). As shown in FIG. 9A, the reduction of clinical scores was significant at day 44 between the 573108 10 mg/kg and Model (P<0.0001) and between Tofacitinib 5 mg/kg and Model (P<0.0001). The P values in the preceding sentence were calculated by ANOVA to compare multiple groups difference which means the pattern was significant.

Results of pairwise analysis of the difference between Model and other groups are listed in Table 3 as follows (M: Model; T: Tofacitinib; S5i: stat5 inhibitor 573108; mpk=mg/kg).

TABLE 3

Pairwise analysis of the difference between groups in the four prophylactic groups.

| | Day 28 | 30 | 32 | 35 | 37 | 39 | 42 | 44 |
|---|---|---|---|---|---|---|---|---|
| M vs T 5 mpk | 0.0949 | 0.0496 | 0.0610 | 0.0064 | 0.0178 | 0.0010 | 0.0015 | 0.0026 |
| M vs S5i 5 mpk | 0.1019 | 0.0410 | 0.0740 | 0.0615 | 0.1101 | 0.0010 | 0.0185 | 0.2729 |
| M vs S5i 10 mpk | 0.1491 | 0.1452 | 0.1256 | 0.0354 | 0.0614 | 0.0008 | 0.0033 | 0.0128 |
| S5i 5 mpk vs S5i 10 mpk | 0.7387 | 0.5943 | 0.8722 | 0.7717 | 0.8686 | 0.9741 | 0.1588 | 0.0717 |

Figure 9B:
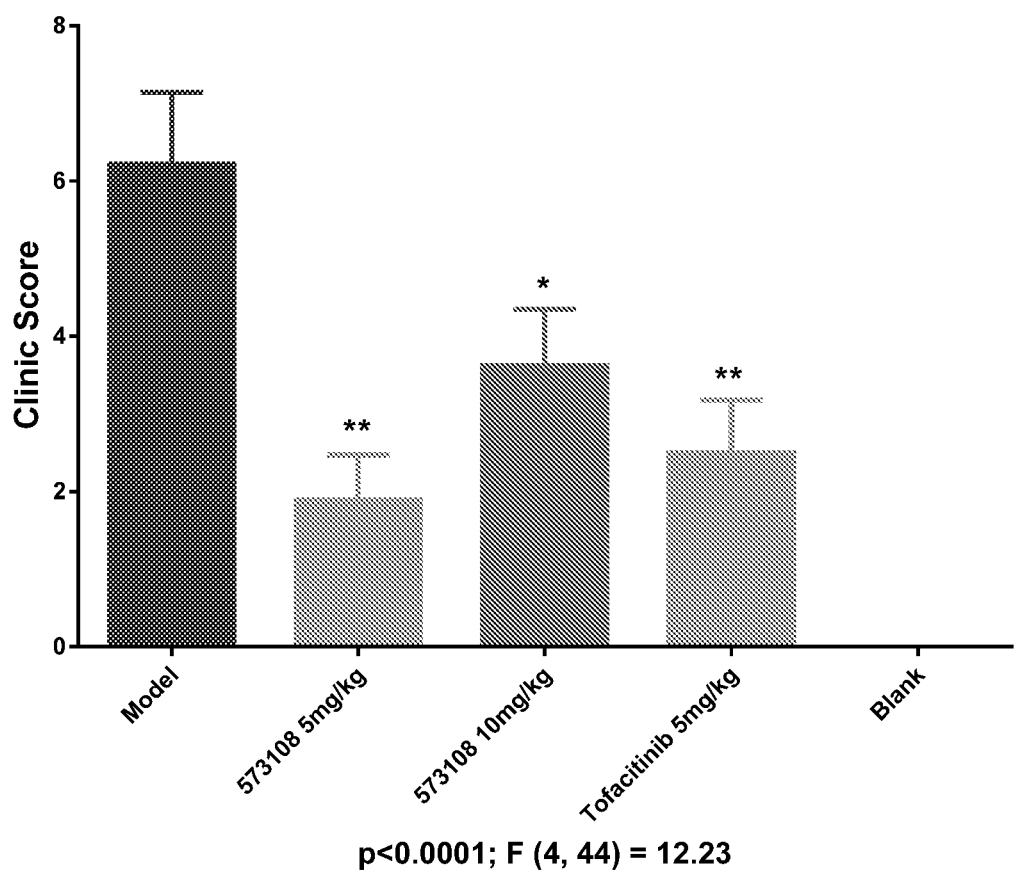

As shown in FIG. 81B, in the CIA induced mice in the four therapeutic groups, compared to the negative controls without treatment (Model), treatment with nicotinohydrazide (573108 10 mg/kg and 573108 5 mg/kg) led to reduced clinical scores similar to the treatment with Tofacitinib (Tofacitinib 5 mg/kg). As shown in FIG. 9B, the reduction of clinical scores was significant at day 44 between the 573108 5 mg/kg and Model (P<0.0001), between the 573108 10 mg/kg and Model (P<0.0001), and between Tofacitinib 5 mg/kg and Model (P<0.0001). The P values in the preceding sentence were calculated by ANOVA to compare multiple groups difference which means the pattern was significant.

Results of pairwise analysis of the difference between Model and other groups are listed in Table 4 as follows (M: Model; T: Tofacitinib; S5i: stat5 inhibitor 573108; mpk=mg/kg).

TABLE 4

Pairwise analysis of the difference between groups in the four therapeutic groups.

| | Day 28 | 30 | 32 | 35 | 37 | 39 | 42 | 44 |
|---|---|---|---|---|---|---|---|---|
| M vs T 5 mpk | 0.0258 | 0.0471 | 0.0138 | 0.0163 | 0.0170 | 0.0153 | 0.0081 | 0.0044 |
| M vs S5i 5 mpk | 0.0117 | 0.0295 | 0.0032 | 0.0025 | 0.0024 | 0.0019 | 0.0044 | 0.0012 |
| M vs S5i 10 mpk | 0.0399 | 0.0190 | 0.0080 | 0.1008 | 0.1336 | 0.1189 | 0.0820 | 0.0397 |
| S5i 5 mpk vs S5i 10 mpk | 0.4163 | 0.8721 | 0.4838 | 0.0249 | 0.0183 | 0.0183 | 0.0777 | 0.0842 |

All references, including publications, patent applications, and patents, cited herein are hereby incorporated by reference to the same extent as if each reference were individually and specifically indicated to be incorporated by reference and were set forth in its entirety herein.

The above description of the disclosed embodiments is provided to enable any person skilled in the art to make or use the present teachings disclosed herein. Various modifications to these embodiments will be apparent to those skilled in the art, and the generic principles described herein can be applied to other embodiments without departing from the spirit or scope of the present teachings. Thus, it is to be understood that the description herein is representative of the subject matter which is broadly contemplated by the present teachings. It is further understood that the scope of the present teachings is not intended to be limited to the embodiments shown herein.

I claim:

1. A method of treating rheumatoid arthritis in a human subject comprising administering to the subject a therapeutically effective amount of a compound, wherein the compound is pimozide or a pharmaceutically acceptable salt of pimozide, wherein said compound is administered to the subject in an amount between about 0.1 mg/kg of body weight per day to about 5 mg/kg of body weight per day.

2. The method of claim 1, where the compound is pimozide.

3. The method of claim 2, wherein pimozide is administered to the subject in an amount between about 1 mg/kg of body weight to about 5 mg/kg of body weight per day.

4. The method of claim 1, wherein the compound is a pharmaceutically acceptable salt of pimozide.

5. The method of claim 1, wherein the subject is an anti-TNF non-responder.

* * * * *